US00PP35878P2

(12) United States Plant Patent
Pavlich

(10) Patent No.: US PP35,878 P2
(45) Date of Patent: Jun. 18, 2024

(54) ***POLEMONIUM* PLANT NAMED 'HURRICANE RIDGE'**

(50) Latin Name: *Polemonium reptans*
Varietal Denomination: Hurricane Ridge

(71) Applicant: Terra Nova Nurseries, Inc., Canby, OR (US)

(72) Inventor: John Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 48 days.

(21) Appl. No.: 18/112,083

(22) Filed: Feb. 21, 2023

(51) Int. Cl.
*A01H 5/02* (2018.01)
*A01H 6/70* (2018.01)

(52) U.S. Cl.
USPC ..... Plt./470
CPC ..... *A01H 6/70* (2018.05)

(58) Field of Classification Search
USPC ..... Plt./470
CPC ..... A01H 5/02
See application file for complete search history.

(56) References Cited

PUBLICATIONS https://www.greenhousecanada.com/perennials-showcase-the-top-picks/; Oct. 26, 2022; 3 pages.*
https://issuu.com/ehrpublications/docs/ehr_hot_new_perennials_2023_7-23-22 _; Aug. 2, 2022; 1 page.*
https://www.bfgsupply.com/media/6179/2022-2023-terra-nova-product-program.pdf; Jun. 10, 2023; 4 pages.*

* cited by examiner

*Primary Examiner* — Kent L Bell
(74) *Attorney, Agent, or Firm* — The Webb Law Firm

(57) ABSTRACT

A new and distinct *Polemonium* plant having a short habit and large, blue flowers with a pale cream eye.

2 Drawing Sheets

Botanical classification: *Polemonium reptans.*
Varietal denomination: 'Hurricane Ridge'.

BACKGROUND OF THE NEW PLANT

The present invention is a new and distinct *Polemonium reptans* plant having the varietal name 'Hurricane Ridge'. *Polemonium* is in the family Polemoniaceae. 'Hurricane Ridge' originated from a controlled cross between unnamed, unpatented, and proprietary *Polemonium* seedlings. The instant plant was selected from a population of seedlings, grown in containers in Canby, Oregon in mid-May of 2021. The new variety was selected for its unique low growing habit, high flower production, and flower size. Compared to the seed parent, the instant plant has larger flowers and a broader habit. Compared to the pollen parent, the instant plant is shorter, with larger and lighter blue flowers.

Compared to *Polemonium* plant named 'Snow and Sapphires' (U.S. Plant Pat. No. 13,441), the new cultivar is low and mounding instead of being upright and tall. Further, the leaves of the new variety are non-variegated and more refined than those of the comparison variety.

Compared to *Polemonium* plant named 'Bambino Blue' (unpatented), the new cultivar is shorter with a broader habit and larger, mid-blue flowers exhibiting a pale cream eye.

The new variety has only been reproduced by asexual propagation (division and tissue culture). Asexual propagation began in July of 2021 in Canby, Oregon. Each of the progeny exhibits identical characteristics to the original plant. Asexual propagation by division and tissue culture performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
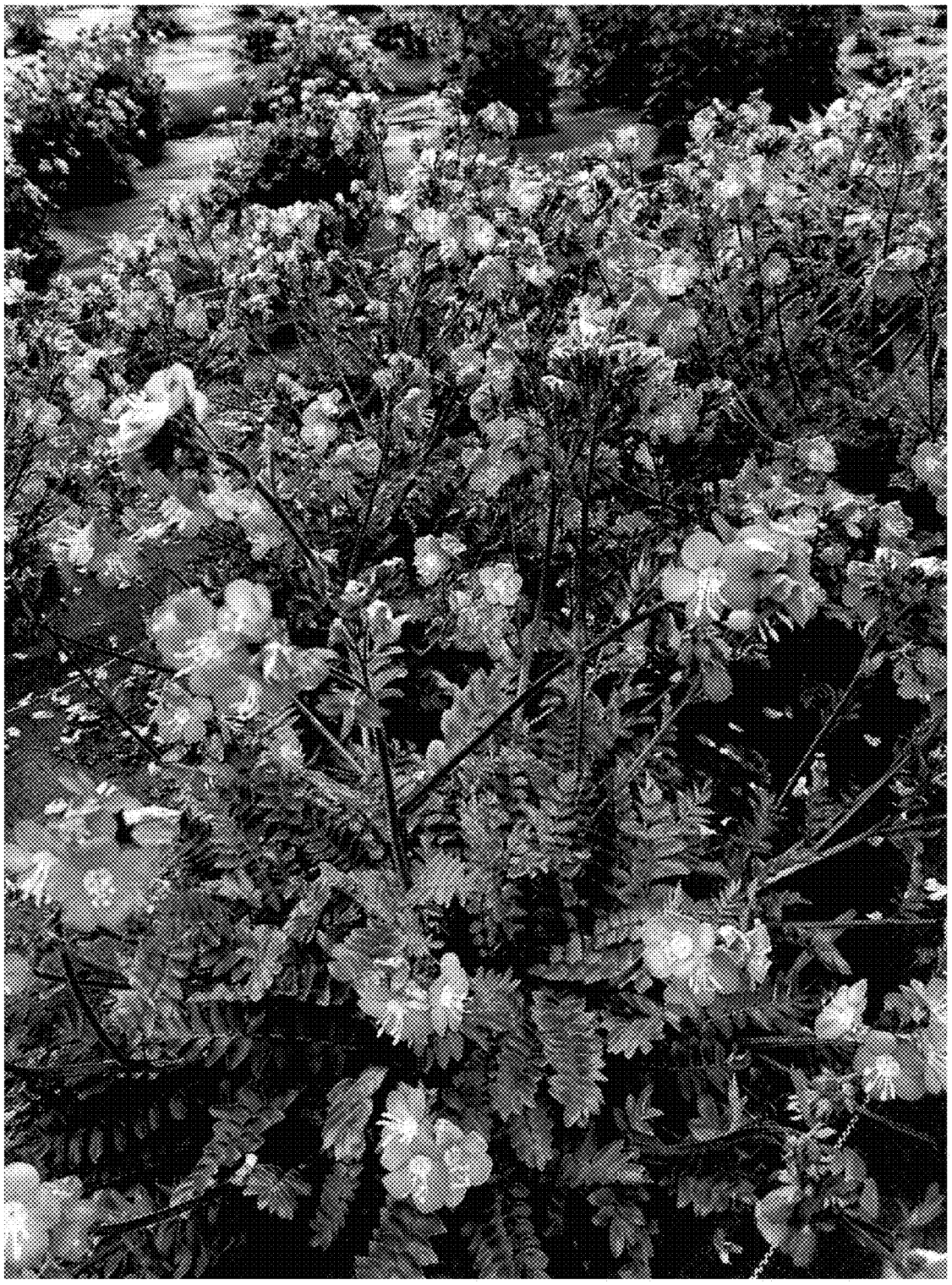
FIG. 1 illustrates a 15-month-old plant of the new variety in Canby, Oregon in May.
Figure 2:
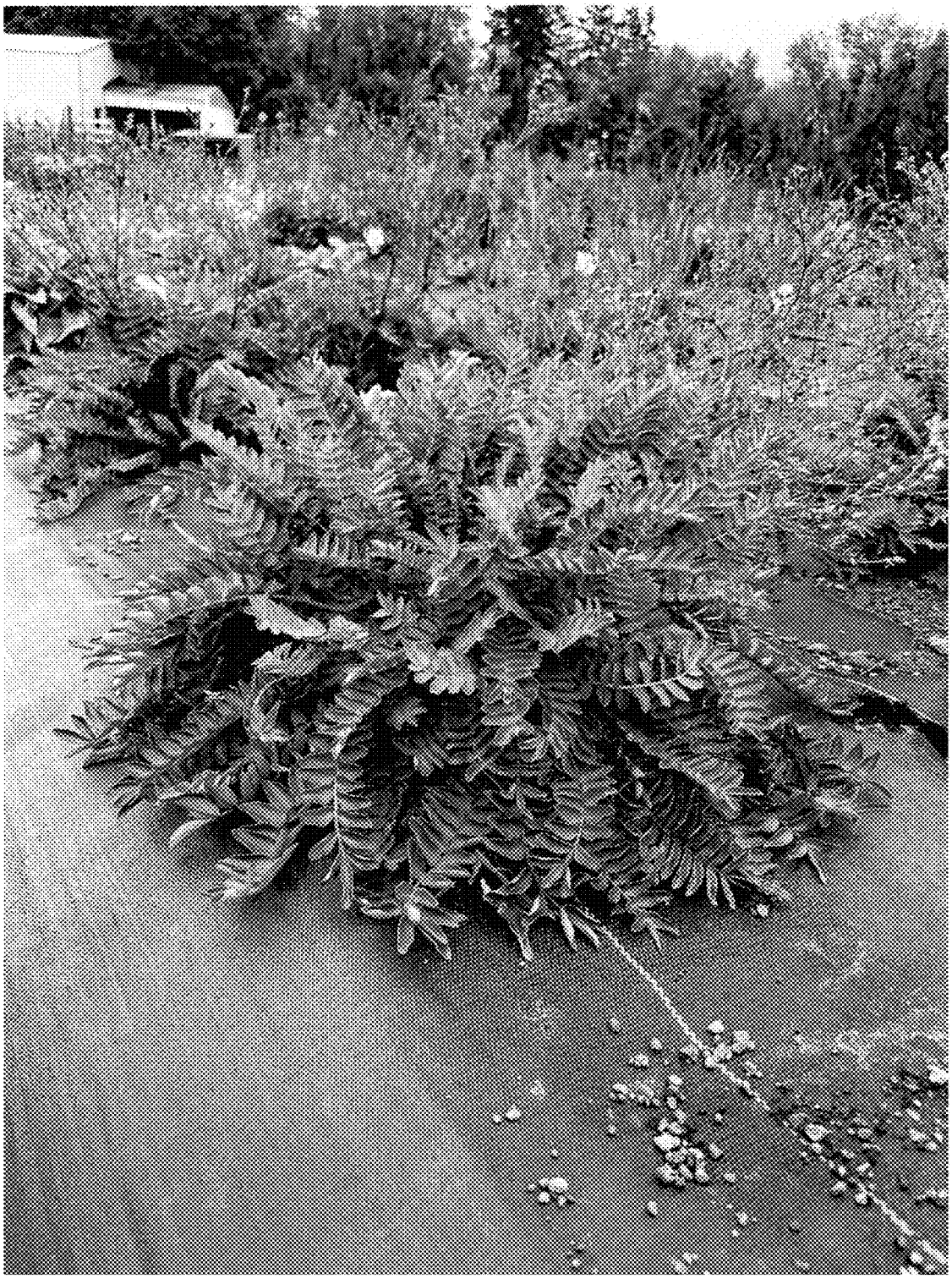
FIG. 2 illustrates a 7-month-old plant of the new variety in Canby, Oregon in September.

The following is a detailed description of the new variety based on observations of 1-year-old plants that were grown outside in Canby, Oregon (USDA Zone 8). Temperatures range from a high of 35° C. in August to an average of 0° C. in January. Normal rainfall in Canby, Oregon is around 1 m per year. Color references are based on the 2007 R.H.S. Colour Chart of The Royal Horticultural Society of London, 5$^{th}$ Edition.

Plant:

*Type.*—Herbaceous perennial.

*Hardiness.*—USDA Zones 3 to 9.

*Size.*—68.0 cm wide and 31.0 cm tall from the top of the soil to the top of the inflorescences in full bloom.

*Form.*—Basal clump.

Leaf:

*Type.*—Pinnately compound; odd to evenly pinnate with 17 to 23 leaflets.

*Arrangement.*—Rosette, with cauline leaves alternate.

*Length.*—13.0 to 17.0 cm.

*Width.*—2.5 to 3.0 cm at the widest part.

*Leaflet.*—Length: 9.5 cm. Width: 2.8 cm. Shape: Ovate. Margin: Entire. Apex: Acute to acuminate. Base: Attenuate.

*Texture.*—Glabrous, very sparsely villous on rachis.

*Venation.*—Pinnate.

*Upper surface color.*—RHS 139B, with margins of RHS N187A.

*Lower surface color.*—RHS N138B.

*Petiole.*—Diameter: 3.5 mm, widening to 4.0 mm at the base. Length: 5.0 cm to sessile, clasping at the base. Texture: Glabrous. Color: RHS 186C at the base, lightening to RHS 186D near the top.

*Petiolules.*—Absent.

*Rachis.*—Length: 8.5 cm. Diameter: 1.5 mm. Color: RHS 145A at apex, darkening to RHS 71A at base. Texture: Glabrous.

Inflorescence:

*Type.*—Terminal corymbose cyme.

*Length.*—40.0 cm.

*Diameter.*—3.0 mm at the apex, widening to 5.0 mm at the base.

*Number per plant.*—About 15.

*Lastingness on the plant.*—About 5 weeks.

*Flower number.*—About 12 to 20 per inflorescence.

*Bloom period.*—April through July in Canby, Oregon, with some repeat blooming in the fall.

*Peduncle.*—Branches: 3 to 5. Length: 29.0 cm. Diameter: 5.0 mm at the base to 3.0 mm at the apex. Texture: Glandular pubescent. Color: RHS 145A, stippled with RHS 187B in the sun.

*Pedicel.*—Length: 8.0 to 10.0 mm. Diameter: 1.0 mm. Texture: Glandular pubescent. Color: RHS 146B.

Flower bud:

*Depth.*—1.0 cm.

*Width.*—0.6 cm.

*Shape.*—Ovate.

*Color.*—RHS N89C.

*Texture.*—Slightly villous and viscous.

Flower:

*Type.*—Actinomorphic.

*Shape.*—Rotate with lobe length exceeding tube length.

*Depth.*—1.0 cm.

*Width.*—2.7 cm.

*Fragrance.*—Sweet, slight incense.

*Lastingness on the plant.*—5-7 days.

*Corolla.*—Arrangement: 5 fused petals. Length: 1.5 cm. Width: 1.0 cm. Apex: Ovate. Base: Rounded. Color: RHS 90A, lightening to RHS 90C near the base and RHS 160A to 155C at the base. Texture: Satiny.

*Calyx.*—Arrangement: 5 lobes, divided 1/3 of the way toward the base. Depth: 9.0 mm. Width: 7.0 mm. Lobe length: 8.0 mm. Apex: Rounded. Margin: Entire. Texture: Glandular pubescent. Color: RHS 144A with tips of RHS N187A.

*Style.*—Length: 6.0 mm. Color: RHS N155A.

*Pistil.*—Number: 1. Length: 7.0 mm.

*Stigma.*—Arrangement: 3 parted. Color: RHS N87A.

*Stamens.*—Number: 5.

*Filament.*—Length: 8.0 mm. Color: RHS N155A.

*Pollen.*—Color: RHS 14A. Quantity: Moderate.

Ovary:

*Shape.*—Ovoid, 3-valved capsule.

*Color.*—RHS 200A.

*Depth.*—3.0 mm.

*Width.*—4.0 mm.

Seeds:

*Fertility.*—Good.

*Shape.*—Sickle.

*Length.*—2.0 mm.

*Color.*—RHS N200A.

Pests/diseases: No unusual resistance or susceptibility noted to date.

I claim:

1. A new and distinct variety of *Polemonium* plant named 'Hurricane Ridge', substantially as illustrated and described herein.

* * * * *